(12) United States Patent
Desai et al.

(10) Patent No.: US 7,879,066 B2
(45) Date of Patent: Feb. 1, 2011

(54) APPARATUS FOR OCCLUDING BODY LUMENS

(75) Inventors: Rupesh Desai, San Jose, CA (US); Alexander L. Huang, Menlo Park, CA (US); Steven Yee, Sunnyvale, CA (US)

(73) Assignee: Percutaneous Sustems, Inc., Palo Alto, CA (US)

( * ) Notice: Subject to any disclaimer, the term of this patent is extended or adjusted under 35 U.S.C. 154(b) by 368 days.

(21) Appl. No.: 11/777,522

(22) Filed: Jul. 13, 2007

(65) Prior Publication Data
US 2009/0018549 A1  Jan. 15, 2009

(51) Int. Cl.
*A61M 29/00* (2006.01)
(52) U.S. Cl. ...................................... 606/200
(58) Field of Classification Search .................. 606/113, 606/114, 127, 198, 200, 213
See application file for complete search history.

(56) References Cited

U.S. PATENT DOCUMENTS

| | | | |
|---|---|---|---|
| 4,046,149 A | 9/1977 | Komiya | |
| 4,262,677 A | 4/1981 | Bader | |
| 4,295,464 A | 10/1981 | Shihata | |
| 4,706,671 A | 11/1987 | Weinrib | |
| 5,135,534 A | 8/1992 | Tulip | |
| 5,192,286 A * | 3/1993 | Phan et al. | 606/127 |
| 5,431,676 A | 7/1995 | Dubrul et al. | |
| 5,454,790 A | 10/1995 | Dubrul | |
| 5,531,717 A | 7/1996 | Roberto et al. | |
| 5,676,688 A | 10/1997 | Jaker et al. | |
| 5,711,841 A | 1/1998 | Jaker | |
| 5,814,058 A | 9/1998 | Carlson et al. | |
| 5,836,913 A | 11/1998 | Orth et al. | |
| 5,897,535 A * | 4/1999 | Feliziani et al. | 604/271 |
| 5,989,264 A | 11/1999 | Wright | |
| 6,007,488 A | 12/1999 | Jaker et al. | |
| 6,056,769 A * | 5/2000 | Epstein et al. | 606/213 |

(Continued)

FOREIGN PATENT DOCUMENTS

DE    10031661 A1    1/2002

(Continued)

OTHER PUBLICATIONS

Bard Urological Division Catalog 1990, PA24, "Woven Blasucci Ureteral Catheters", 3 pages.

(Continued)

*Primary Examiner*—Todd E Manahan
*Assistant Examiner*—Naquan Ishman
(74) *Attorney, Agent, or Firm*—Townsend and Townsend and Crew LLP

(57) ABSTRACT

A luminal occlusion device comprises a tension member, an elongate shaft, and a flat film having an axial receptacle which is received over a distal portion of the tension member. The flat film has proximal and distal ends which are attached to the distal ends of the tension member and the elongate shaft, respectively. Thus, distal advancement of the tension member relative to the shaft will cause the flat film to assume a low profile configuration, while proximal retraction of the tension member relative to the elongate shaft will cause the flat film to assume a foreshortened, compacted configuration. The film usually includes one or more radioopaque markers which help shape the compacted film.

23 Claims, 4 Drawing Sheets

U.S. PATENT DOCUMENTS

| | | | |
|---|---|---|---|
| 6,080,174 A | 6/2000 | Dubrul et al. | |
| 6,214,037 B1 | 4/2001 | Mitchell et al. | |
| 6,240,968 B1 | 6/2001 | Bigonzi-Jaker et al. | |
| 6,325,812 B1 | 12/2001 | Dubrul et al. | |
| 6,494,893 B2 | 12/2002 | Dubrul et al. | |
| 6,500,182 B2 * | 12/2002 | Foster | 606/127 |
| 6,520,983 B1 * | 2/2003 | Colgan et al. | 623/1.11 |
| 6,656,146 B1 | 12/2003 | Clayman et al. | |
| 6,780,197 B2 * | 8/2004 | Roe et al. | 606/213 |
| 6,929,664 B2 | 8/2005 | Kolb | |
| 6,945,950 B2 | 9/2005 | Clayman et al. | |
| 7,044,134 B2 * | 5/2006 | Khairkhahan et al. | 128/887 |
| 7,052,507 B2 * | 5/2006 | Wakuda et al. | 606/194 |
| 7,214,229 B2 | 5/2007 | Mitchell et al. | |
| 7,217,250 B2 | 5/2007 | Kolb | |
| 7,229,461 B2 * | 6/2007 | Chin et al. | 606/198 |
| 2001/0044595 A1 | 11/2001 | Reydel et al. | |
| 2002/0183853 A1 | 12/2002 | Mitchell et al. | |
| 2003/0120281 A1 | 6/2003 | Bates et al. | |
| 2005/0197627 A1 | 9/2005 | Huang et al. | |
| 2005/0228481 A1 | 10/2005 | Manasas et al. | |
| 2007/0173882 A1 * | 7/2007 | Spurchise | 606/200 |
| 2007/0191768 A1 | 8/2007 | Kolb | |

FOREIGN PATENT DOCUMENTS

EP  0 605 427 B1  12/1992

OTHER PUBLICATIONS

Garrido et al., "Utilización del catéter "stone sweeper" en la patologia litiásica del tracto urinario superior," [The use of Stone Sweeper catheter for stone disease of the upper urinary tract], Arch Esp Urol. 2006, Nov; 56(9):889-892. [English Abstract Only]

L'Esperance et al., "Ureteral Expanding Stent: A New Device for Urolithiasis," J Endourol. May 1, 2007; 21(5): 533-537.

Woitzik et al., "Polyethylene sheath device to reduce tumor cell seeding along the needle tract in percutaneous biopsy," (2003) Surg. Endosc. 17:311-314.

* cited by examiner

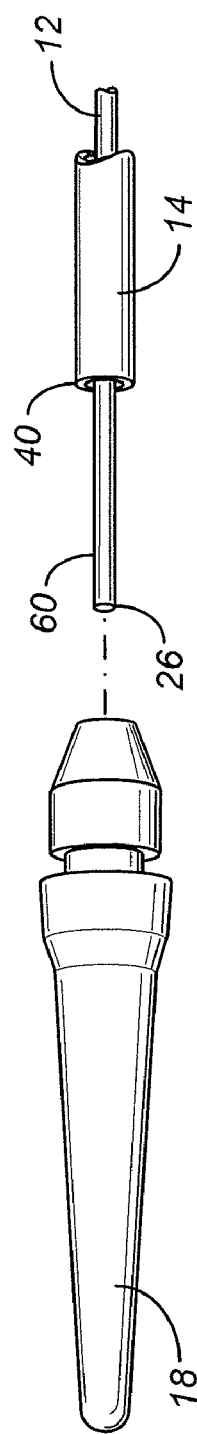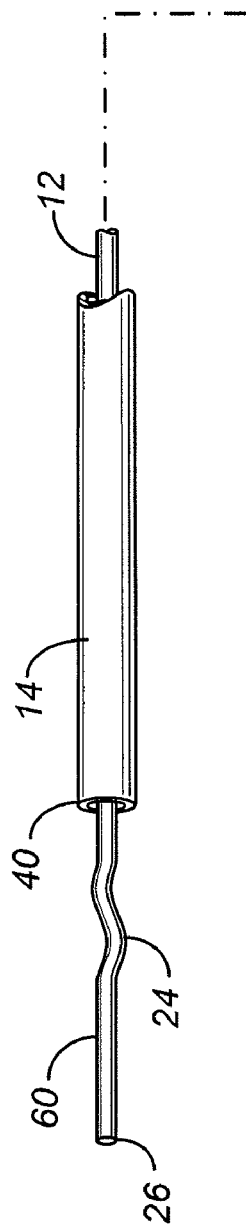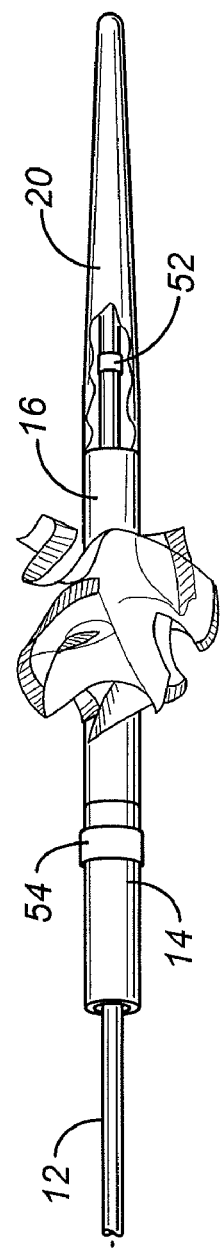
FIG. 4
FIG. 5

APPARATUS FOR OCCLUDING BODY LUMENS

CROSS-REFERENCES TO RELATED APPLICATIONS

The present application is related to but does not claim the benefit of copending application Ser. No. 10/886,886, filed on Jul. 7, 2004 and Ser. No. 11/777,515, filed on the same day as the present application, the full disclosures of which are incorporated herein by reference.

BACKGROUND OF THE INVENTION

1. Field of the Invention

The present invention relates generally to medical apparatus. More particularly, the present invention relates to apparatus for treating ureters and other body lumens.

It is common for kidney stones to pass from the kidney through the ureter to the urinary bladder. While muscular peristalsis of the ureter will often pass the stones into the bladder without complication, in some instances large and/or irregularly shaped stones may become lodged within the ureter causing discomfort and potential damage to the ureter and upper collective system.

A number of ways have been proposed for dislodging such kidney stones. For example, extracorporeal shock wave lithotripsy (ESWL) can be used to break up the kidney stones but is often ineffective when the stones are present in the ureter. Moreover, ESWL can produce irregularly-shaped fragments which, while smaller than the original stone, may have sharp edges that will prevent spontaneous passage of the particles through the ureter. In the case of a stone or fragment impacted in the ureter, it is common practice to attempt capture, using a wire stone basket. The basket is introduced through a ureteroscope which itself is typically introduced retrograde through the urinary tract.

In many cases, further lithotripsy through the scope is performed (ISWL). It is often difficult to advance such stone baskets past the obstructing material. Attempts to pass wire baskets or other grasping apparatus past a stone lodged in the ureter also presents risk of damage to the ureter. Abrasion, stretching, or perforation of the ureter at the impaction site can cause local urine leakage or edema even if the stone or resulting debris is successfully captured; and removal of the basket with the stone may be quite difficult. In some instances, baskets containing captured stones or fragments cannot themselves be removed, and it is difficult if not impossible to release the captured stone material back into the lumen of the ureter. In those cases, the basket must often be retrieved surgically. Finally, if and/or when ISWL is performed, it would be useful to have some means of stabilizing stone fragments at the treatment site, rather than letting them escape up the ureter in a retrograde direction.

As an improvement over lithotripsy and the use of baskets for collecting kidney stones and debris, it has recently been proposed to use a compacted length of material to form an occluding structure within a ureter. The compacted length of material can be used to either directly draw and remove the kidney stone from the ureter into the bladder. Alternatively, the compacted length of material can be used to contain fragments which are produced in an energy-based lithotripsy procedure. As described in prior copending application Ser. No. 10/866,866, the length of material can be an everting tubular member, a flat membrane which folds as an accordion structure, can or take a variety of other configurations. None of the prior described occlusion structures, however, has been optimum in all respects.

For these reasons it would be desirable to provide improved apparatus for deploying and compacting a length of material in order to occlude a body lumen, such as a ureter, when performing procedures for the removal and/or lithotripsy of kidney stones. In particular, it would be desirable to provide apparatus having material lengths which may be delivered in a very low profile configuration while permitting deployment into a relatively high volume configuration having a substantial density and ability to conform to symmetric and non-symmetric body lumens to help assure effective occlusion of the body lumen, particularly occlusion of ureters to prevent the passage of kidney stones and kidney stone fragments. The apparatus should also be atraumatic in use, require significantly less skill than basket manipulation, optionally allow the release of captured material, should be simple and economical in construction and use, and should provide minimum risk and trauma to the patient. At least some of these objectives will be met by the inventions described hereinbelow.

2. Description of the Background Art

The use of an everting sleeve composed of thin, tensilized polytetrafluoroethylene for introducing catheters to body lumens is described in U.S. Pat. Nos. 5,531,717; 5,676,688; 5,711,841; 5,897,535; 6,007,488; 6,240,968; and EP605427B1. A wire basket for preventing stone fragment movement through a body lumen during lithotripsy procedure is available under the Stone Cone tradename from Boston Scientific Corporation. See Published U.S. Application No. 2003/0120281. Copending application Ser. No. 10/794,337, filed on Mar. 5, 2004, the full disclosure of which is incorporated herein by reference, describes a sheet delivery system that could be used in performing some of the methods described herein.

BRIEF SUMMARY OF THE INVENTION

The present apparatus provides an improved luminal occlusion device, comprising a tension member, an elongate shaft, and a flat film having an axial receptacle for receiving a distal portion of the tension member. The tension member has a proximal end and a distal end, and is typically formed as a solid core wire having the dimensions and properties generally associated with smaller guidewires, such as uretal guidewires. The elongate shaft serves as a guide structure for the tension member and will usually comprise a hollow tube, such as a hollow polymeric tubular body, having a distal end and a proximal end. The tension member is slidably received within a lumen of the elongate shaft, and the distal end of the tension member is able to extend distally from the distal end of the shaft and axially translate relative to the elongate shaft. The axial receptacle of the flat film will then be disposed over the tension member and will typically have a proximal end fixed or otherwise coupled to a distal end of the elongate shaft and a distal end fixed or otherwise coupled to a distal location on the tension member. Thus, the flat film can be axially elongated and placed in a low profile configuration by advancing the tension member distally relative to the elongate shaft. Conversely, the flat film can be compacted into a high volume configuration by proximally drawing the tension member relative to the elongate shaft. By having the axial receptacle of the film positioned over the tension member, the symmetry of the deployment is improved.

In particular embodiments of the present invention, the flat film has characteristics which are further selected to improve the symmetry and effectiveness of the deployment. For example, flat film will typically have parallel edges which are spaced apart by a distance in the range from 2 mm to 15 mm and will have a length in the axial direction in the range from 10 cm to 100 cm. Preferred flat films will comprise one or more polymeric sheet(s) having a total thickness in the range from 0.1 mm to 0.5 mm. It has been found that sheets with these characteristics will have a very low profile elongated configuration to facilitate introduction into the body lumen, particularly into ureters and past kidney stones, as well as having a deployed, high-volume configuration which is symmetric and particularly suitable for deployment and occlusion within a ureter.

In another particular aspect of the present invention, the flat film will comprise at least one radioopaque marker formed therein or on a surface thereof. Typically, the marker will be located along at least one of the axial edges (e.g., parallel to and spaced inwardly from the edge), and more typically, one marker will be provided along each of the two edges of the flat film. In most preferred embodiments, flat film includes a first wing portion formed on one side of the axial receptacle and a second wing portion formed on the other side of the axial receptacle. A first elongate radioopaque marker is disposed along an outer edge of the first wing and a second radioopaque marker is disposed along an outer edge of the second wing. In some embodiments, two or more markers may be placed in parallel and/or in series along the edge(s). Particularly suitable radioopaque markers are metal strips, in particular being gold foil strips.

In a specific embodiments, the radioopaque markers may have different mechanical properties than those of the film. In particular, the markers may be more rigid or stiff than the film, causing the film to collapse or fold in a manner different from what would occur without the marker. For example, the metal foil markers disposed along opposite edges of the film will cause the film to rotate as it collapses, thus forming a higher volume and less collapsible occlusion than would be formed with a simple accordion-type fold. Gold foil is an ideal material for this application as it is dense and highly radioopaque, can be utilized as a very thin foil, and while being stiffer than the thin film, is still quite flexible. However, other materials in strips, films, foil, or wires could also be utilized, with or without requiring high radioopacity. For example, thin shape memory wires, such as nickel titanium wires, could be pre-shaped or "programmed" to take a particular shape or to fold in a particular sequence/shape when released from tension, and put under compression. Shaping of the compacted film could also be accomplished by screening a relatively thick layer of ink on the film in strips or in a geometric pattern.

In certain embodiments of the present invention, the luminal occlusion device will further comprise a distal tip extending distally from the distal end of the tension member. The distal tip will be relatively soft and facilitate atraumatic introduction on the occlusion device through a body lumen, particularly through a ureter past a kidney stone. Usually, the distal tip will comprise a polymeric tube which tapers down in the distal direction, and the polymeric tube will comprise a polymer, such as polyurethane, having a durometer in the range from 25 D to 55 D.

The tension member will typically comprise a solid core wire, usually having a width in the range from about 0.2 to about 0.6 mm. In other cases, however, the tension member could comprise a hollow core wire, could have dimensions which are larger or smaller than those cited above.

In preferred aspects of the present invention, the elongate shaft will comprise a polymeric tube having an outside width in the range from 0.5 mm to 1.5 mm and a length in the range from 50 cm to 250 cm. The polymeric tube may comprise any of a variety of polymers, typically being a polyether block amide having a durometer in the range from 50 D to 80 D. In many cases, at least a portion of the polymer tube will be reinforced, and in particular embodiments the entire polymeric tube is reinforced with a steel braid.

The occlusion device will typically have a handle at or near its proximal end. In preferred embodiments, the handle is removably attachable to the proximal end of the elongate shaft and is positioned over a proximal end of the tension member. In such cases, the handle allows manipulation of the occlusion device while it is being introduced into the ureter or other body lumen. The handle also prevents accidental deployment of the tension member since it covers and protects the distal end. Thus, in use, the handle will be moved after the occlusion device has been positioned within the body lumen at its target location. After the handle is removed, the proximal end of the tension member is exposed so that the user may manually grasp the proximal end, and pull on it in a proximal direction in order to deploy the flat film. Usually, the proximal end of the tension member will be modified to provide a gripping surface to facilitate manual deployment.

In still further aspects of the present invention, the tension member may be modified or additional components provided in order to lock or hold the flat film in its deployed configuration after the tension member has been pulled proximally. For example, a detent structure may be formed at or near the proximal end of the tension member, where the detent expands when the tension member is proximally retracted to deploy the film. The expanded detent thus blocks or inhibits inadvertent distal movement of the tension member which would unintentionally return the flat film to its low profile configuration. The detent may comprise, for example, a bend in the tension member, such as a short serpentine section.

BRIEF DESCRIPTION OF THE DRAWINGS

FIGS. 4 and 5 illustrate the steps which are taken to deploy a flat film on the luminal occlusion device of FIGS. 1 and 2.

DETAILED DESCRIPTION OF THE INVENTION

Figure 1:
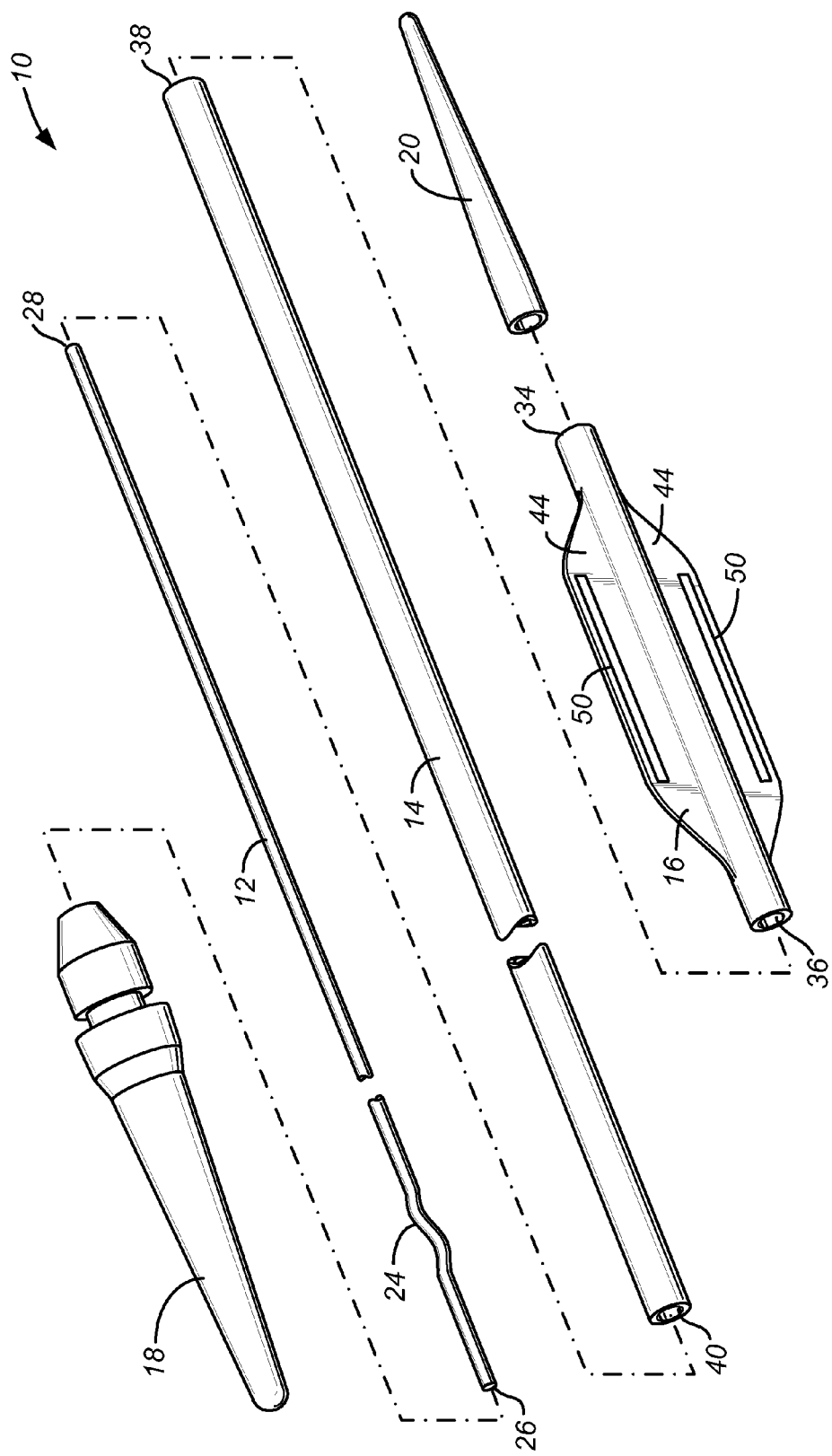
FIG. 1 is an exploded view of a luminal occlusion device constructed in accordance with the principles of the present invention.
Figure 2:
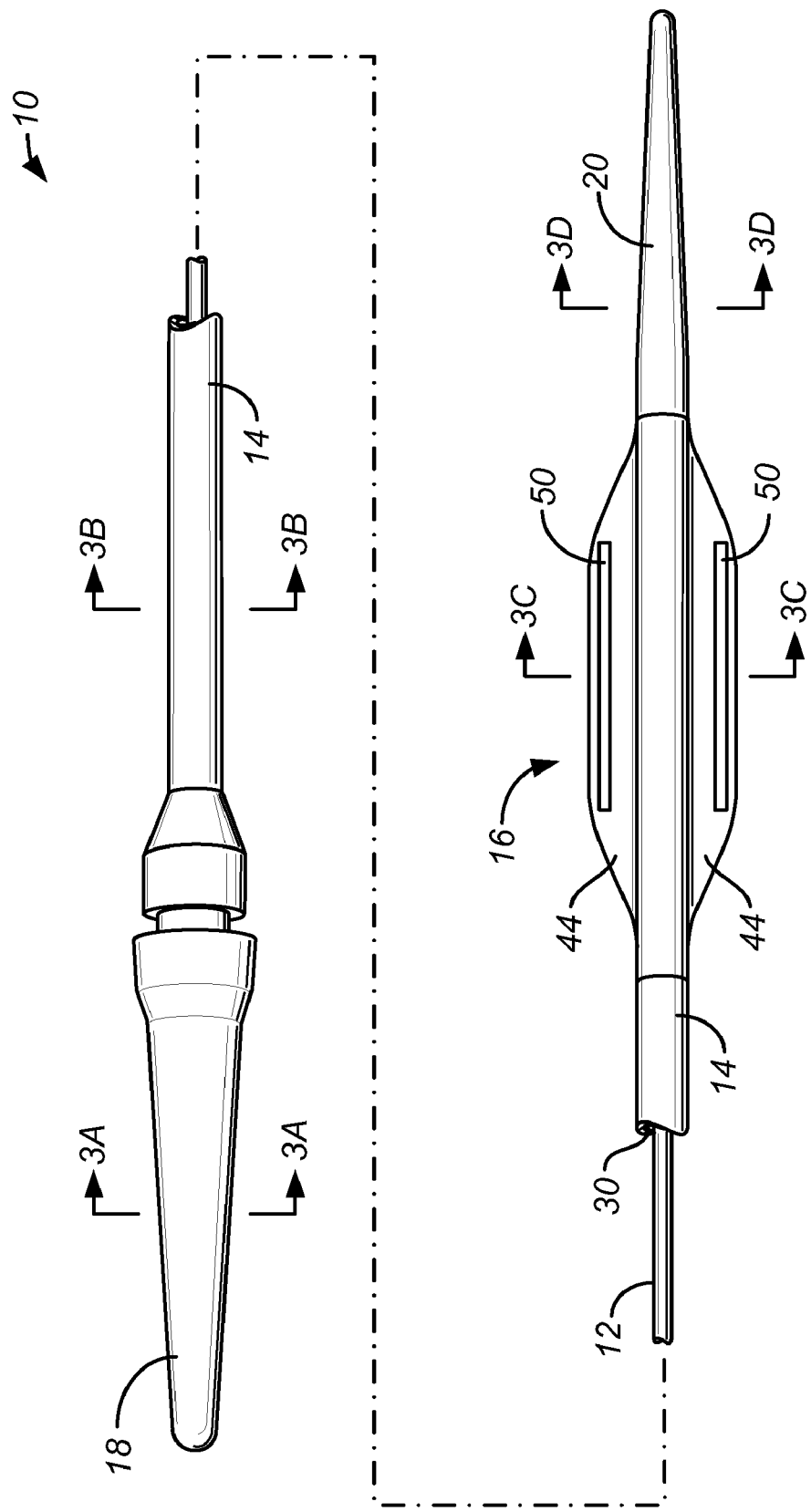
FIG. 2 illustrates the luminal occlusion device of FIG. 1 in its assembled configuration with portions broken away.
Figure 3A:
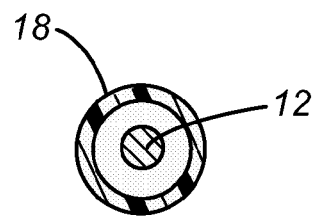
FIGS. 3A-3D are cross-sectional drawings taken along lines 3A to 3D in FIG. 2.
Figure 3B:
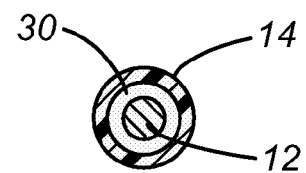
Figure 3C:
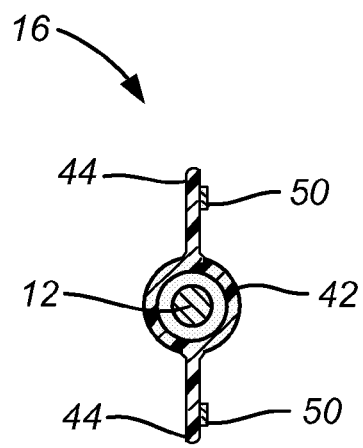
Figure 3D:
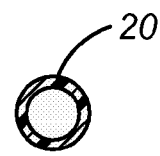

As illustrated in FIGS. 1, 2, and 3A-3D, an exemplary luminal occlusion device 10 constructed in accordance with the principles of the present invention, comprises a tension member 12, an elongate shaft 14, a flat film 16, a handle 18, and a distal tip 20. The tension member 12 comprises a solid core wire, typically composed of stainless steel or nickel-titanium alloy, having a length in the range set forth above. A serpentine detent 24 is formed near a proximal end 26 thereof. The distal end 28 of the tension member will pass through a lumen 30 of the elongate shaft 14, as best seen in FIGS. 2 and 3B. The distal end 28 is connected to a distal end 34 of the flat film 16, while a distal end 38 of the elongate shaft 14 is connected to a proximal end 36 of the flat film. The distal portion of the tension member 12 passes through an axial receptacle 42 of the flat film 16, as best seen in FIG. 3C, and proximal retraction of the tension member 12 relative to elongate shaft 14 will thus cause the axial receptacle 42 to bunch up on the tension member, thus compacting the opposed wings 44, causing them to deploy, as best illustrated in FIG. 5 discussed below. A pair of radioopaque markers 50 are formed on the flat film 16, typically being gold foil strips which are glued, bonded, or otherwise attached to the wings 44. Additional radioopaque markers 52 and 54 are formed on the distal ends of the tension member 12 and elongate shaft 14, respectively. The distal tip 20 is also attached to the distal end 28 of the tension member 12, although the tip will usually have a hollow lumen, as best seen in FIG. 3D.

The flat film 16 on the luminal occlusion device 10 may be deployed in a simple, two-step procedure. As illustrated in FIG. 4, the handle 18 is first removed from the proximal end 40 of the elongate shaft 14, exposing a gripping surface 60 at the proximal end 26 of the tension member 12. The user may then deploy the film 16 by grasping the elongate shaft 14 near the proximal end 40 with one hand and grasping the gripping surface 60 on the tension member 12 with the other hand. The gripping surface 60 is then proximally withdrawn relative to the elongate shaft 14 which causes the distal end 28 of the tension member to move toward the distal end 38 of the elongate shaft. This foreshortening causes the film 16, which is captured between these two ends, to axially shorten and compact, as shown in FIG. 5. As the distal end 28 of the tension member 12 is drawn proximally relative to the elongate shaft 14, the radioopaque markers 52 and 54 can be observed to move toward each other and will define the leading and trailing ends of the film 16 after it is compacted. The combination of the flat film and the axial markers, preferably having a stiffness greater than that of the film, causes a high volume and resilient structure which is capable of conforming to and effectively occluding the body lumen deployment, as illustrated.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A luminal occlusion device comprising: a tension member having a proximal end and a distal end; an elongate shaft having a guide structure along at least a distal portion thereof for receiving the tension member and permitting the tension member to shift between a distally extended position and a proximally retracted position relative to the shaft; and a flat film consisting essentially of a polymeric sheet structure having a total thickness in the range from 0.1 mm to 0.5 mm having an axial receptacle for receiving a distal portion of the tension member wherein a distal end of the film is attached to a distal location on the tension member and one wing extending radially outwardly from opposite sides of the axial receptacle and a proximal end of the film is attached to a distal end of the elongate shaft, wherein proximally translating the tension member relative to the shaft compacts the flat film and distally translating the tension member relative to the shaft stretches the film.

2. A device as in claim 1, wherein the flat film has parallel axial edges spaced apart by a distance in the range from 2 mm to 15 mm.

3. A device as in claim 2, wherein the flat film has a length in the axial direction in the range from 10 cm to 100 cm.

4. A device as in claim 1, wherein the flat film comprises at least one radioopaque marker formed on a surface thereof.

5. A device as in claim 4, wherein the flat film comprises at least two radioopaque markers, with one disposed on each side of the axial receptacle.

6. A device as in claim 5, wherein a first elongate radioopaque marker is disposed along an outer edge of one of the wings and a second radioopaque marker is disposed along an outer edge of the other wing.

7. A device as in claim 6, wherein the radioopaque markers comprise gold foil strips.

8. A device as in claim 1, further comprising a distal tip extending distally from the distal end of the tension member.

9. A device as in claim 7, wherein the distal tip comprises a polymeric tube which tapers down in the distal direction.

10. A device as in claim 8, wherein the polymeric tube comprises polyurethane having a durometer in the range from 25 D to 55 D.

11. A device as in claim 1, wherein the tension member comprises a solid core wire.

12. A device as in claim 11, wherein the wire comprises stainless steel with a width in the range from 0.2 mm to 0.6 mm.

13. A device as in claim 1, wherein the elongate shaft comprises a polymeric tube having an outside width in the range from 0.5 mm to 1.5 mm and a length in the range from 50 cm to 250 cm.

14. A device as in claim 13, wherein the polymeric tube comprises polyether block amide having a durometer in the range from 50 D to 80 D.

15. A device as in claim 14, wherein at least a portion of the polymeric tube is reinforced.

16. A device as in claim 15, wherein the entire length of the polymeric tube is reinforced with a steel braid.

17. A device as in claim 1, further comprising a handle assembly at the proximal end of the elongate shaft.

18. A device as in claim 17, further comprising a grip at the proximal end of the tension member.

19. A device as in claim 18, wherein the handle is removably attached to the proximal end of the shaft and the grip can be covered by the handle when the tension member is positioned fully distally relative to the shaft.

20. A device as in claim 1, further comprising a detent near the proximal end of the tension member, wherein the detent expands when the tension member is proximally retracted to deploy the film and wherein the expanded detent inhibits inadvertent distal movement of the tension member after deployment.

21. A device as in claim 20, wherein the detent comprises one or more bend in the tension member.

22. A device as in claim 1, further comprising at least one reinforcement element on the flat film, wherein the reinforcement element causes the film to collapse in a high volume configuration as the film is compacted.

23. A device as in claim 22, wherein the reinforcement comprises radioopaque markers.

\* \* \* \* \*